United States Patent [19]

Sylvanowicz

[11] Patent Number: 5,267,982
[45] Date of Patent: Dec. 7, 1993

[54] VARIABLE SHAPED CATHETER SYSTEM AND METHOD FOR CATHETERIZATION

[75] Inventor: John T. Sylvanowicz, Andover, Mass.

[73] Assignee: C. R. Bard, Inc., Murray Hill, N.J.

[21] Appl. No.: 542,157

[22] Filed: Jun. 8, 1990

Related U.S. Application Data

[63] Continuation-in-part of Ser. No. 188,046, Apr. 29, 1988, Pat. No. 4,935,017.

[51] Int. Cl.⁵ .................................................. A61M 25/00
[52] U.S. Cl. ................................. 604/281; 604/53; 604/256; 604/280
[58] Field of Search ............................ 604/51–53, 604/156–170, 280–284, 43, 264, 95, 171, 256; 128/656–658, 772

[56] References Cited

U.S. PATENT DOCUMENTS

| | | | |
|---|---|---|---|
| 3,856,009 | 12/1974 | Winnie | 604/201 |
| 4,033,331 | 7/1977 | Guss et al. | 604/281 |
| 4,117,836 | 10/1978 | Erikson | 604/281 |
| 4,136,681 | 1/1979 | Hon | 128/2 R |
| 4,169,464 | 10/1979 | Obrez | 604/281 |
| 4,430,083 | 2/1984 | Ganz et al. | 604/283 |
| 4,547,193 | 10/1985 | Rydell | 604/282 |
| 4,563,181 | 1/1986 | Wijayarathna et al. | 604/280 |
| 4,581,017 | 4/1986 | Sahota | 604/281 |
| 4,616,652 | 10/1986 | Simpson | 128/344 |
| 4,694,838 | 9/1987 | Wijayarthna et al. | 604/281 |
| 4,738,667 | 4/1980 | Galloway | 604/281 |
| 4,795,434 | 1/1989 | Kujawski | 604/159 |
| 4,810,244 | 3/1989 | Allen | 604/44 |
| 4,822,345 | 4/1989 | Danforth | 604/282 |
| 4,828,550 | 5/1989 | Kurimoto | 604/171 |
| 4,909,777 | 3/1990 | Danforth | 604/282 |
| 4,935,017 | 6/1990 | Sylvanowicz | 604/280 |
| 4,976,691 | 12/1990 | Sahota | 128/772 |
| 5,120,323 | 6/1992 | Shockey et al. | 128/657 |

FOREIGN PATENT DOCUMENTS

| | | |
|---|---|---|
| 0092389 | 4/1983 | European Pat. Off. . |
| 0249456 | 6/1987 | European Pat. Off. . |
| 0256478 | 8/1987 | European Pat. Off. . |
| 0278937 | 2/1988 | European Pat. Off. . |
| 2627851 | 6/1976 | Fed. Rep. of Germany . |
| 2923633 | 12/1980 | Fed. Rep. of Germany . |

*Primary Examiner*—C. Fred Rosenbaum
*Assistant Examiner*—Mark Bockelman
*Attorney, Agent, or Firm*—Wolf, Greenfield & Sacks

[57] ABSTRACT

A catheter assembly and method for catheterization provides a means by which the curved configuration at the distal portion of a catheter can be varied while the catheter system remains in the patient. The catheter, having a predetermined curve at its distal end is received within a sheath that can be advanced over the distal end to tend to straighten the curve in the distal end of the catheter. The extent to which the sheath is advanced over the curved distal portion of the catheter controls the degree to which the catheter is straightened. The position of the sheath relative to the catheter can be adjusted while the catheter is in the patient, thereby enabling change in catheter shape without requiring catheter exchanges. For example, the system enables right and left coronary angiographic procedures to be performed without changing catheters. Left ventricular studies also can be made without catheter exchanges.

18 Claims, 5 Drawing Sheets

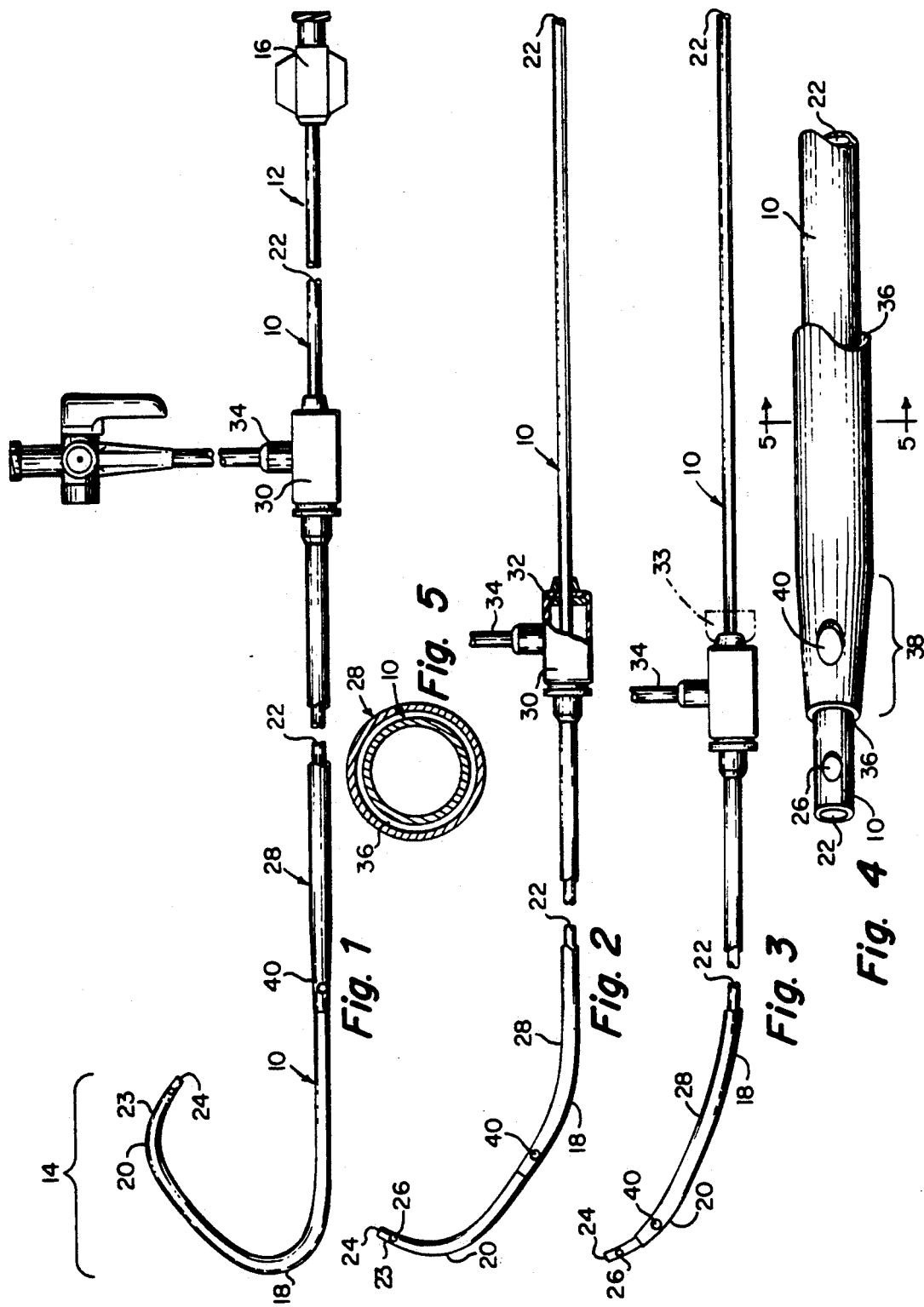

VARIABLE SHAPED CATHETER SYSTEM AND METHOD FOR CATHETERIZATION

RELATED APPLICATION

This application is a continuation in part of U.S. application Ser. No. 188,046 filed Apr. 29, 1988 now U.S. Pat. No. 4,935,017.

FIELD OF THE INVENTION

This invention relates to improved angiographic and cardiovascular catheter systems and methods of catheterization.

BACKGROUND OF THE INVENTION AND PRIOR ART

For many years it has been the common practice in angiographic and cardiovascular procedures to use various angiographic catheters having different distal tip shapes in order to perform various angiographic studies. For example, when performing coronary angiography, it is common to perform studies of the left coronary artery, the right coronary artery, and the left ventricle by injecting X-ray opaque contrast liquid into each of the right and left coronary arteries and also into the left ventricle. Each injection is done with a separate catheter having a specially formed distal tip adapted to facilitate entry into the ostium of the right or left coronary artery. Typically, a catheter having a pigtail shape is used for left ventricular studies. In order to perform these studies it has been the typical practice to exchange catheters for each study. That is time consuming and subjects the patient to the trauma of multiple catheter insertion and removal. Additionally, the use of multiple catheters increases the risk of a blood clots and, in general, presents greater risk for complications.

The desirability of reducing the time involved in performing such angiographic studies as well as minimizing trauma to the patient by making a catheter having a tip shape adjustable while in the patient has been suggested in the prior art. U.S. Pat. No. 4,033,331 to Guss discloses a specially formed catheter having two lumens, including a main lumen through which the radiopaque contrast liquid may be injected into the blood vessel and another lumen which receives a relatively stiff elongated contour wire. The distal end of the catheter has a predetermined curved shape which can be progressively straightened by advancing the contour wire distally through its lumen. The system discussed in the Guss patent has several disadvantages, the principal one being that it cannot be used with a conventional angiographic catheter. The practice of the technique disclosed in the Guss patent requires the use of the special two lumen catheter construction. That catheter construction necessarily has reduced flow area in the main lumen because of the necessity of providing the cross-sectional area for the contour wire lumen. Because it is important to maintain as large a flow area as possible in an angiographic catheter so that the radiopaque contrast liquid can be injected at a relatively high flow rate. The two lumen catheter construction comprises that desirable feature.

SUMMARY OF THE INVENTION

In accordance with one aspect of the present invention an angiographic catheter assembly is provided which includes a flexible angiographic catheter of conventional construction having a full size lumen and a pre-shaped curve at its distal end. The catheter extends through a sheath that is several centimeters shorter than the catheter, by an amount at least as great as the length of the curved distal segment of the catheter. The shape of the curve at the distal end of the catheter can be varied by advancing the sheath over the catheter. The sheath has sufficient stiffness so that it tends to straighten the catheter curve as it advances over it, thereby progressively changing the shape of the curve. The catheter assembly enables a method of angiography by which different procedures can be performed on the patient without requiring catheter exchanges for each procedure.

In another aspect of the invention, the sheath also may be used to deliver fluids or make pressure measurements at the distal tip of the sheath. To this end the proximal end of the sheath may be provided with a fitting having a side leg for liquid infusion. The inner diameter of the sheath may be somewhat larger than the outer diameter of the catheter to define an annular flow space along the length of the assembly. It is desirable that the distal tip of the sheath fit closely to the outer diameter of the catheter, the tip of the sheath being tapered for this purpose. In order to provide for fluid communication at the distal end of the sheath, the sheath may be provided with several side holes at its distal end. In addition, the sheath may be used as an introducer should it be desired to remove the catheter and replace it with another catheter.

The system is used in a method in which the relative position of the sheath on the catheter is selected to place the distal end of the catheter in a particular curved configuration suited for the angiographic procedure to be performed. After the dye injection and procedure have been completed, the longitudinal position of the sheath with respect to the catheter may be adjusted either to increase or decrease the curvature at the distal end or to permit the catheter to assume its more curved relaxed configuration, depending on which procedure is next to be performed. The change in configuration is effected quickly and simply with no additional trauma to the patient and without increasing the risk of complications that may result from a succession of catheter exchanges.

In another embodiment of the invention, the sheath and catheter are formed so that the primary bend is formed in the sheath and the secondary bend is formed in the catheter. In this embodiment, the catheter, in its relaxed configuration, is straight along its full length except for its distal tip, which is bent approximately at a right angle to define the distal, secondary bend of the assembly. The distal portion of the sheath is formed with a larger radius bend, approximately 180°. When the inner catheter and outer sheath are assembled, with the inner catheter extending through the sheath, the secondary bend is disposed entirely outside of the sheath and the cooperation between the normally straight inner catheter and sharply bent sheath results in a primary, large radius curve for the assembly that is less than 180°. In this configuration, the assembly defines somewhat of a Judkin's left curvature adapted to access easily the entry to the left coronary artery. Because the inner catheter is independently movable and rotatable with respect to the outer sheath, this embodiment of the invention is convertible to a configuration adapted to engage the right coronary artery with simple, easy manipulations. Thus, this embodiment of the invention may be made to intubate the right coronary artery by manipulations that include rotating the inner catheter about 180° so that its distal tip points away from the left coronary ostium and toward the right coronary ostium and partially withdrawing the outer sheath. The position and configuration of the catheter assembly is such that the rotation of the inner catheter and withdrawal of the outer sheath brings the distal tip of the inner catheter into engagement with the right coronary ostium.

It is among the general objects of the invention to provide an improved catheter system for performing multiple cardiovascular and angiographic procedures while minimizing or reducing catheter exchanges.

Another object of the present invention is to provide a catheter system and method for catheterization by which the curvature at the distal end of a cardiovascular or angiographic catheter may be adjusted quickly and simply while within the patient.

Another object of the invention is to provide a system of the type described which, in one embodiment, utilizes a conventional angiographic catheter having a full size flow lumen.

A further object of the invention is to provide a catheter system of the type described in which the degree of curvature at the distal region of the catheter is controlled by a sheath that is slidably received over the catheter and which can be advanced or withdrawn over the catheter.

Another object of the invention is to provide a system of the type described in which means are provided for injecting radiopaque contrast liquid and making pressure measurements at the distal end of the sheath.

A further object of the invention is to provide system of the type described in which the sheath also may serve as a catheter introducer should it be desired to make a catheter exchange.

Another object of the invention is to provide an angiographic curvature having primary and secondary bends in which the portion of the primary bend along the catheter can be varied.

Still another object of the invention is to provide a two piece angiographic catheter in the form of a inner catheter and an outer sheath and in which a primary curve is formed in the sheath and a secondary curve is formed in the inner catheter.

DESCRIPTION OF THE DRAWINGS

The foregoing and other objects and advantages of the invention will be appreciated more fully from the following further description thereof, with reference to the accompanying drawings wherein:

FIG. 1 is a fragmented illustration of the catheter system in accordance with the invention.

FIG. 2 is an illustration of the system with the sheath advanced distally over the primary curve in a Judkins left coronary catheter;

FIG. 3 is an illustration similar to FIG. 2 but with the sheath advanced over the secondary curve of the angiographic catheter;

FIG. 4 is an enlarged illustration of the distal end of the sheath and catheter;

FIG. 5 is a sectional illustration as seen along the line 5—5 of FIG. 4;

DESCRIPTION OF THE PREFERRED EMBODIMENT

Figure 6:
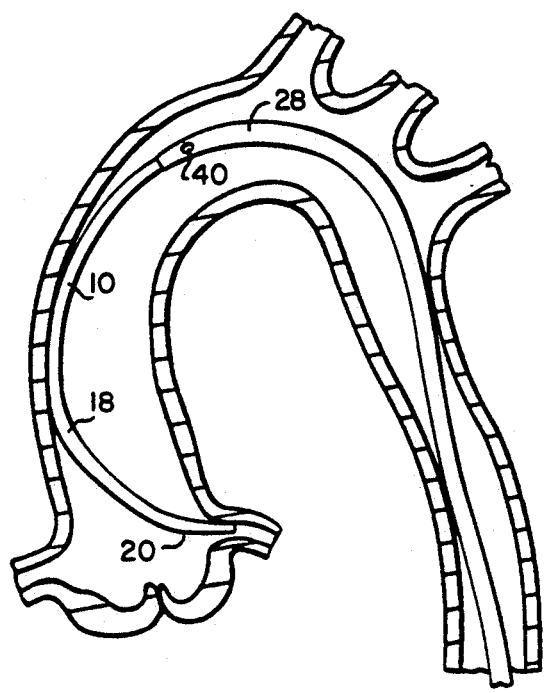
FIG. 6 is a diagrammatic illustration of the embodiment of FIG. 1 placed in a patient with the tip of the catheter intubating the left coronary artery.

The system illustrated includes an angiographic catheter 10 having a proximal end 12 and a distal end 14. The proximal end is provided with a fitting 16 which can be connected to a syringe for injecting radiopaque contrast liquid through the catheter 10 and into the patient. The distal end 14 of the catheter 10 is formed to define a predetermined curvature and, in one illustrative embodiment (FIG. 1), the curvature is that conventionally known as the left Judkins curve, adapted for use in left coronary artery angiography. The left Judkins shape may be considered as having a primary curve 18 and a secondary curve 20. A lumen 22 extends fully through the angiographic catheter 10, from the fitting 16 to the distal outlet tip 24. The lumen 22 is full diameter, that is, it is uncompromised by the presence of any other elements in the catheter. The construction of the catheter 10 may be conventional as will be appreciated by those skilled in the art. For example, the catheter may be formed from extruded plastic material and may have woven or braided elements embedded in the catheter wall. By way of example the catheter may be approximately 125 centimeters in length although the length may be varied depending on the specific type of angiographic or cardiovascular procedure that is to be employed. If desired, the distal tip of the angiographic catheter 10 also may be provided with side holes 26 as seen in FIG. 2 to increase outlet capacity. Typically, the tip of the catheter 10 will be tapered as indicated at 23 so that it may fit closely about a guidewire extending through the lumen 22 for smooth percutaneous entry, as will be appreciated by those familiar with the art.

The system of the present invention also includes an outer sheath indicated generally by the reference character 28 through which the catheter 10 extends. The sheath is circular in cross-section, as is the catheter 10, and may be formed from an appropriate extruded tube, such as FEP or PTFE fluorinated polymer. The sheath 28 is several centimeters shorter than the catheter 10, by an amount at least equal to the length of the curved distal portion 14 of the catheter 10. In the illustrative embodiment, the sheath is between 5 and 30 centimeters, preferably approximately 10 centimeters shorter than the catheter. Typically, the sheath length will be between 30 to 150 cm, depending on the length of the catheter. The proximal end of the sheath may be provided with a hemostasis fitting 30 that receives the catheter 10 and includes an internal proximal gasket 32 (FIG. 2) that engages the outer surface of the catheter 10 to form a seal against the catheter 10. The fitting 30 may be provided with an adjustable gasket such as a Tuohy-Borst adapter (illustrated in phantom at 33 in FIG. 3) by which the constricting force of the gasket about the catheter may be varied thereby to vary the degree with which the gasket seals against the catheter. The fitting 30 also may be provided with a side leg 34 through which liquids may be injected, pressure measurements may be made and sampling performed. The side leg on the sheath fitting also may be used to aspirate if there is to be a catheter exchange, in order to withdraw embolisms, or to inject heparin.

In the embodiment of FIG. 1, the sheath is formed so that when it is advanced over the curved distal portion 14 of the catheter 10, the stiffness of the sheath will cause the curve in the angiographic catheter 10 to become somewhat straighter. To this end, the sheath should be formed from a material and should have a wall thickness and stiffness sufficient to cause the catheter to assume the particular desired shape. FIG. 2 shows a sheath in an extended position in which it has been advanced over the primary curve 18 of the Judkins left catheter. In this configuration, the catheter is suited somewhat for a right coronary arteriography procedure. FIG. 3 illustrates the configuration of the system with the sheath advanced over both the primary and the secondary curves 18, 20 respectively. In this configuration, the assembly is best suited for an arteriography of coronary artery by-pass or for left ventriculography in the angiographic procedure. By way of example the catheter 10 may be between about 0.052 to about 0.117 (4F to 9F) in outer diameter and may be formed from polyurethene material with a braided tubular element embedded therein. The sheath preferably is formed from a tube of Teflon fluorinated polymer also in a 4F to 9F size with an inside diameter to match and receive the catheter. The sheath also preferably is radiopaque, as by incorporating barium sulfate or some other suitable radiopaque material into the polymer.

Figure 7:
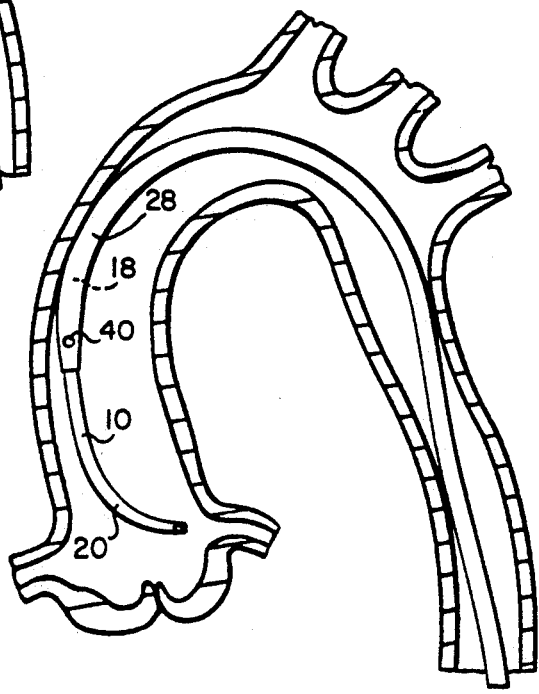
FIG. 7 is an illustration similar to FIG. 6 with the sheath advanced over the primary curve of the catheter to a configuration better adapted to intubate the right coronary artery.
Figure 8:
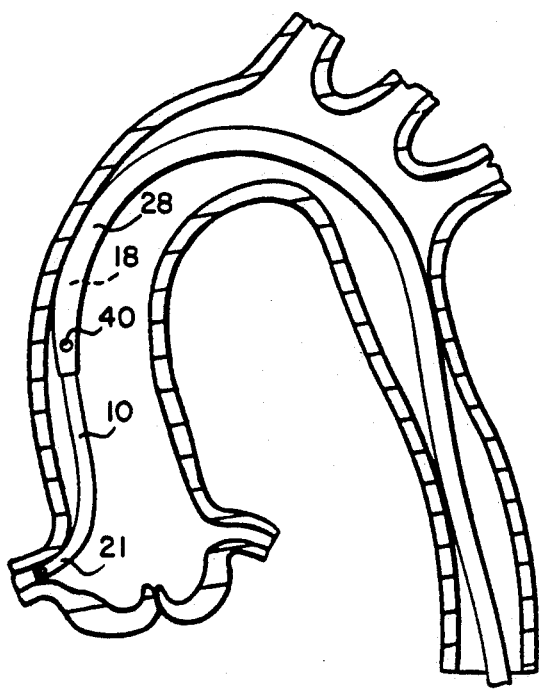
FIG. 8 is an illustration of the catheter arrangement of FIGS. 6 and 7 with the catheter having been rotated approximately 180° in a position to intubate the right coronary artery.

FIGS. 6–8 illustrate the manner in which the above-described embodiment may be used first to perform angiography in the left coronary artery and then in the right coronary artery without removing the catheter assembly from the patient. FIG. 6 shows the distal portion of the catheter, with the sheath withdrawn proximally of the primary curve 18 so that the catheter 10 may assume its relaxed or near relaxed configuration. As will be appreciated by those familiar with coronary angiography, the Judkin's left configuration shown in FIG. 6 is adapted to cause the distal tip of the catheter to intubate the left coronary ostium (the entrance to the left coronary artery). After an angiography study has been completed on the left coronary artery, the catheter may be reconfigured, while remaining in the patient, to somewhat of a Judkin's right configuration. That may be achieved by advancing the sheath 28 over the catheter and over the primary curve 18 to tend to straighten out the catheter 10 and reduce the sharpness of the primary bend 18. FIG. 7 indicates somewhat of a configuration of the catheter assembly with the sheath so advanced. The catheter assembly then is rotated about its axis by the physician approximately 180°, as is common procedure with a standard Judkin's right catheter, as will be apparent to those familiar with coronary angiography. Once rotated, the distal tip of the catheter will tend to intubate the right coronary ostium, as shown in FIG. 8. The right coronary angiography procedure then may proceed.

FIGS. 4 and 5 illustrates a tip construction for the sheath in which the sheath is adapted to provide fluid communication between its proximal and distal ends while receiving the catheter In this embodiment the inner diameter of the sheath is somewhat larger than the outer diameter of the catheter to define an annular flow area 36 that communicates with the side leg 34. In the illustrated embodiment the tip of the sheath is tapered as indicated at 38 and fits closely against the outer surface of the catheter 10 to facilitate percutaneous introduction of the entire systems as a unit into the patient s blood vessel. One or more side holes 40 may be formed adjacent the tip of the sheath to provide for fluid communication with the annular area 36. The foregoing arrangement enables infusate to be delivered, pressure recordings to be made as well as sampling and purging. It may be noted that the distal portion of the sheath may have a straight configuration when relaxed or itself may be provided with a pre-formed curve.

The foregoing system also enables pressure differentials to be measured across a patient's aortic valve. By locating the system so that the distal tip of the catheter is located distally of the aortic valve and with the side holes 40 at the distal end of the sheath 28 located proximally of the aortic valve, pressure measurements can be made on both sides of the valve thereby providing an indication of the pressure differential.

Figure 9:
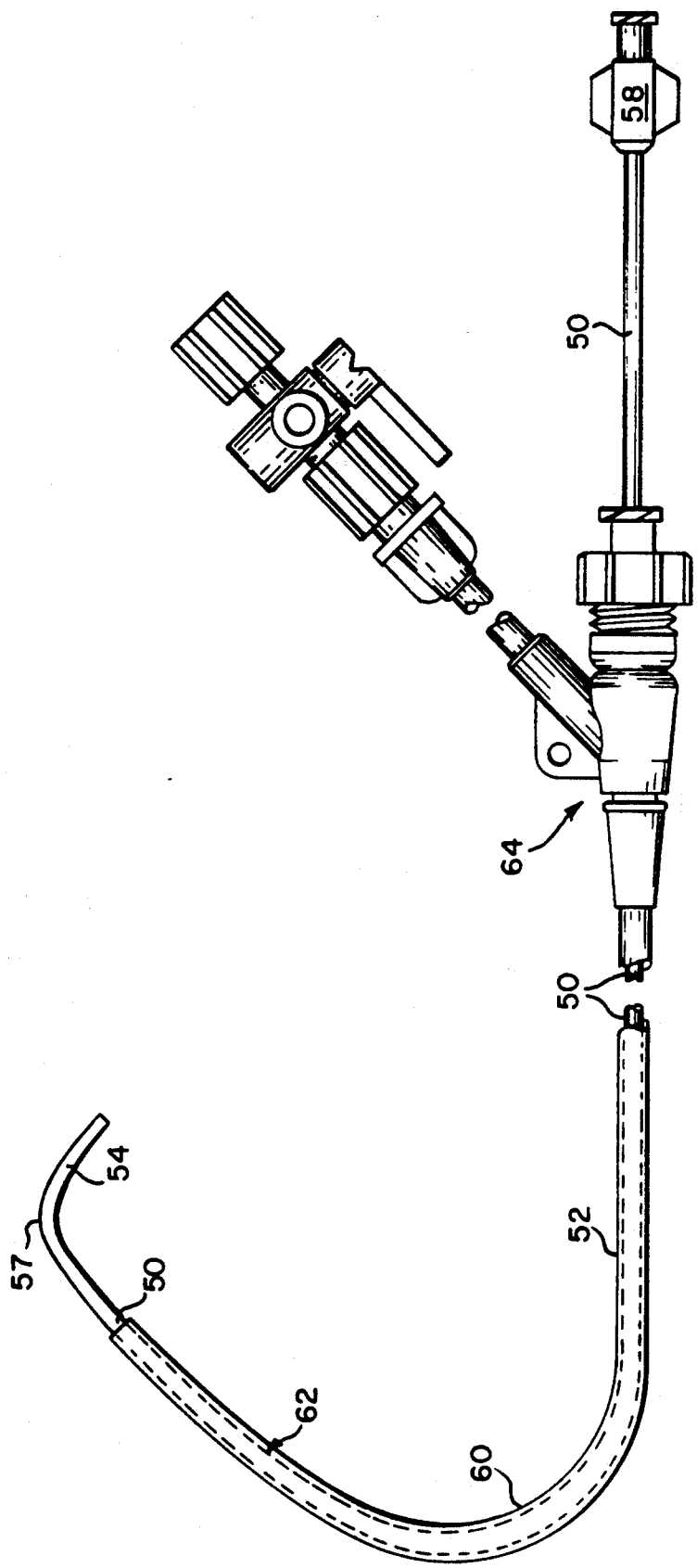
FIG. 9 is an illustration of another embodiment of the invention including an inner catheter and an outer tubular sheath.
Figure 11:
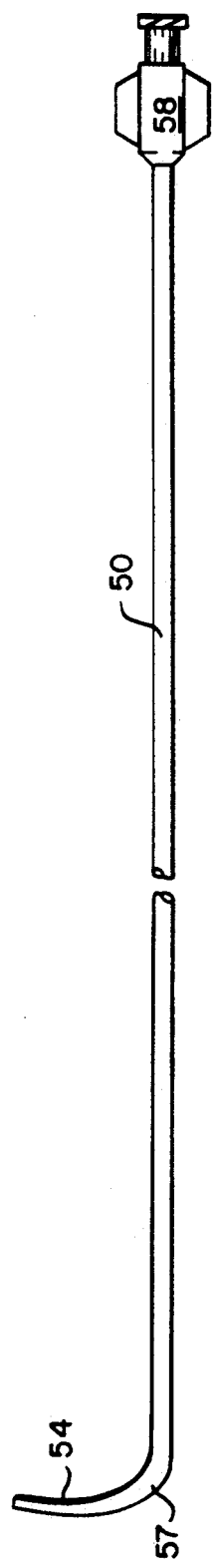
FIG. 11 is an illustration of the inner catheter of the assembly illustrated in FIG. 9.

FIG. 9 illustrates another embodiment of the invention in which the torque required to rotate the catheter to engage the right coronary artery is reduced. In this embodiment one of the curves is formed in the sheath and the other is formed in the inner catheter. More particularly, this embodiment includes an inner catheter 50 and an outer sheath 52. The inner catheter is illustrated itself in FIG. 11. It may be formed from the same material as the catheter 10 in the first described embodiment. The inner catheter 50 is straight except for its distal tip which may be curved at substantially a right angle to define a transversely extending tip segment 54. The inner catheter 50 is hollow and has a luer fitting 58 attached to its proximal end for connection to a liquid injection device, such as a syringe or the like. The outer sheath 52 may be formed from the same material as the outer sheath 28 in the first described embodiment. The outer sheath has a relatively large radius curve 60 formed adjacent its distal end and a straight distal segment 62 extending from the curved portion 60. The relatively sharp radius bend 57 in the catheter will define the secondary curve of the catheter assembly and the larger radius curve in the sheath cooperates with the catheter 50 to define the primary bend 60 as indicated in FIG. 9.

Figure 10:
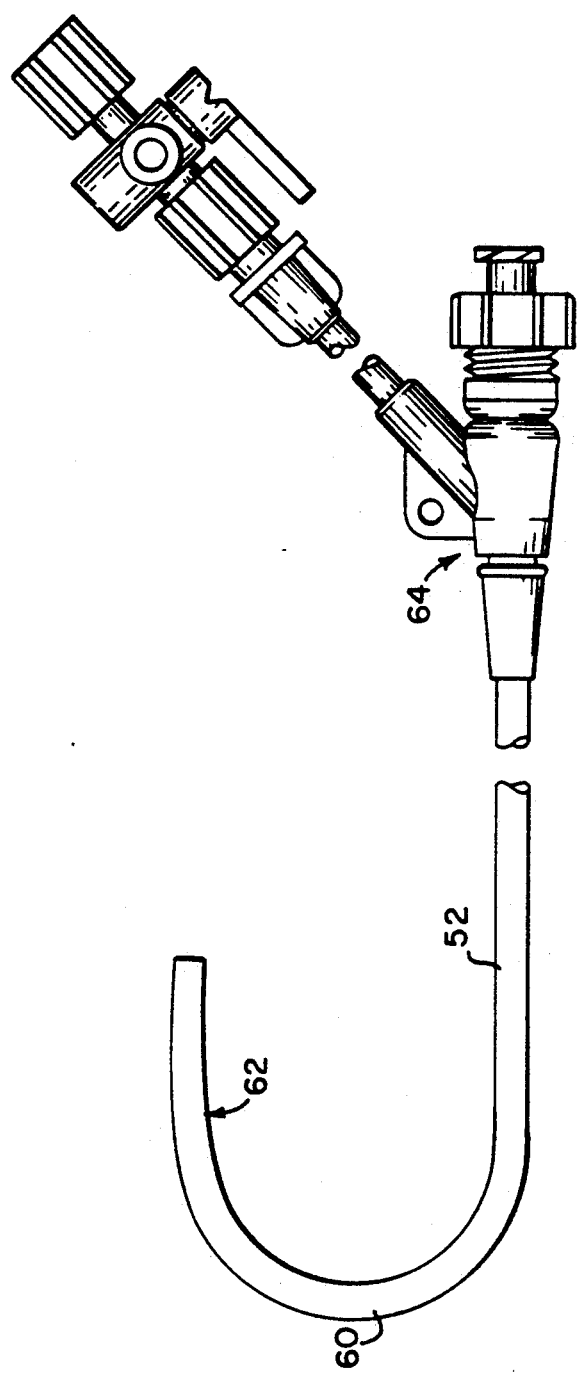
FIG. 10 is an illustration of the outer sheath of the assembly illustrated in FIG. 9.

As can be seen from a comparison of FIGS. 9 and 10 when the catheter 50 is extended through and projects distally from the distal end of the outer sheath 52, the angle defined by the primary curve 60 is somewhat greater than the angle when the sheath is in a relaxed configuration (FIG. 10). By way of example, the curve 60 in the relaxed sheath may define an angle of about 180° whereas that angle may increase to about 140° when the catheter 50 extends through the sheath. Thus, from FIG. 9 it will be appreciated that the distal end of the assembled inner catheter 50 and outer sheath 52 define, generally, a somewhat modified Judkin's left configuration in that the angle defined by the bend 60 is somewhat greater than the angle in a conventional Judkin's left which is approximately 180° (relaxed).

As with the first described embodiment, the proximal end of the sheath preferably has a fitting 64 attached thereto. The fitting 64 includes a hemostasis valve (not shown) as described above in connection with the first embodiment to effect a seal between the catheter 50 and fitting 64. A side arm port 66 also may be provided for the same purposes and functions described above in connection with the first embodiment.

Among the advantages of this embodiment of the invention is that the orientation of the distal tip 54 may be varied by rotating the proximal end of the catheter 50 by the fitting 58. Thus, the inner catheter may be rotated along its longitudinal axis so that it is directed selectively toward the left coronary ostium or the right coronary ostium. Additionally, the configuration of the distal portion of the catheter assembly may be controlled by withdrawing the catheter sheath proximally over the inner catheter. Such withdrawal shifts the location of the primary curve proximally along the length of the catheter which causes a repositioning of the distal portion of the inner catheter so that it points toward the right coronary ostium.

Figure 12:
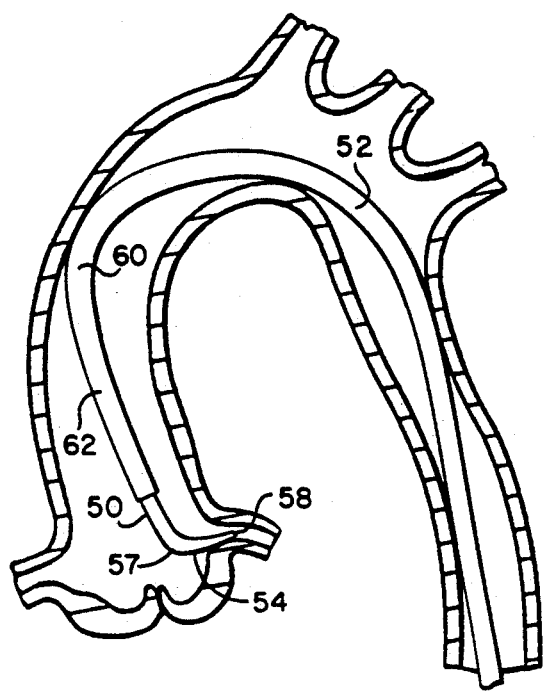
FIG. 12 is an illustration of the embodiment shown in FIG. 9 advanced into position to intubate the left coronary artery.
Figure 13:
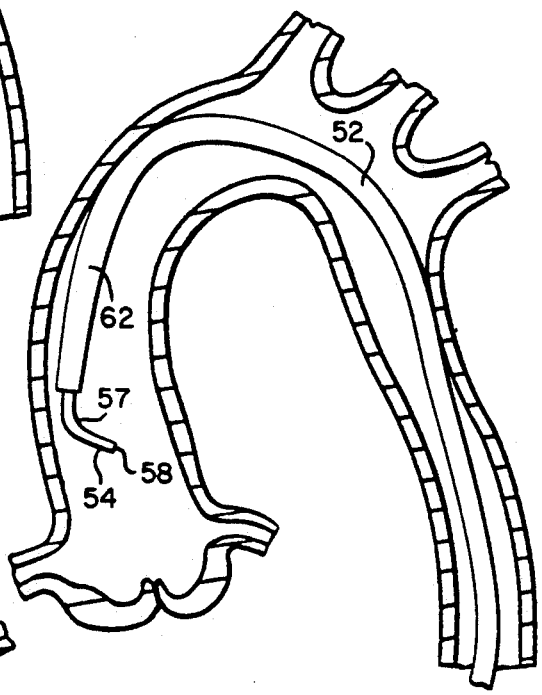
FIG. 13 is an illustration of the catheter of FIG. 12 with the catheter withdrawn to reposition the primary curve of the catheter in a more proximal location.
Figure 14:
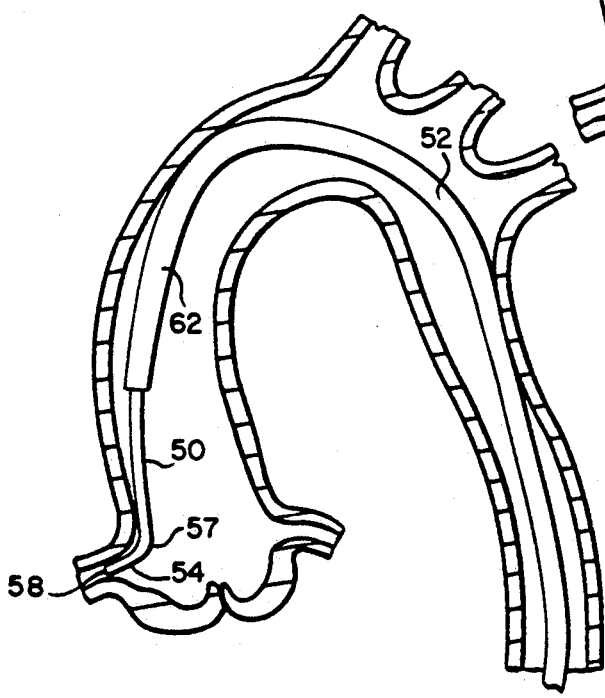
FIG. 14 is an illustration of the manner in which the catheter assembly of FIG. 13 is manipulated to convert it to a right coronary configuration, with the inner catheter extended and showing it intubated in the right coronary artery.

The use of the embodiment of FIG. 9 is illustrated in FIGS. 12–14. FIG. 12 shows the catheter assembly placed in the patient's aorta with the tip segment 58 of the inner catheter 50 intubated in the left coronary ostium. After the angiographic study of the left coronary artery has been completed, the right coronary artery may be studied by manipulating the catheter assembly to intubate the distal end 58 of the inner catheter 50 in the right coronary artery ostium as shown in FIG. 14. With this embodiment, that is achieved simply and quickly as illustrated in FIGS. 13 and 14 by combined withdrawal of the sheath 52 and rotation of the inner catheter 50. Thus, as illustrated in FIG. 13, the sheath 52 has been withdrawn so that the position of the primary curve relative to the distal end of the catheter is moved proximally. By withdrawing the sheath proximally to reposition the primary curve, the distal segment 62 is reoriented and points toward the right coronary ostium. Thus, when extended, the position of the protruding distal portion of the inner catheter shifts from the position as shown in FIG. 12 toward a position toward the right coronary ostium. The inner catheter 50 may be rotated about its longitudinal axis approximately 180° to direct the distal tip 58 toward the right coronary ostium so that as the distal portion of the catheter 50 continues to shift it will bring the tip 58 into the right coronary ostium. It may be noted that it is a significant feature of this embodiment that by forming the primary curve on the sheath and the secondary curve on the catheter, there is less resistance to rotation of the system to orient the tip 58 toward the right coronary ostium. In this embodiment, it is not necessary to rotate both inner catheter and outer sheath portions of the catheter assembly. Consequently, there is less resistance to rotation and the procedure may be accomplished with greater ease.

It will be appreciated that the system may be percutaneously introduced and used by advancing into the patients blood vessels in a conventional manner as is well known to those skilled in the art. The sheath may be positioned along the catheter to present the desired curved configuration for the first study to be performed. After that study is performed the relative position of sheath and catheter may be adjusted to change the configuration of the catheter distal curve without requiring catheter exchanges. Dye injections and pressure measurements also may be made through the side leg 34 of the sheath if desired. Should it be desired to perform catheter exchanges that is facilitated by the sheath which may be permitted to remain in the patient's blood vessel thereby to serve as a catheter introducer. The system utilizes a full bore angiographic catheter and thus permits full flow of radiopaque contrast liquid into the patient's blood vessels.

It should be understood, however, that the foregoing description of the invention is intended to be illustrative and that other modifications and embodiments may be apparent to those skilled in the art without departing from its spirit and scope as set forth in the appended claims.

Having thus described the invention what I desire to claim and secure by letters patent is:

1. A variable shape angiographic catheter assembly comprising;
    a flexible elongated inner catheter having a proximal end and a distal end, the catheter having a secondary curve formed at its distal end to define an offset distal tip segment;
    a flexible tubular sheath having a proximal end and a distal end and an internal diameter adapted to receive the inner catheter and to enable longitudinal movement of the inner catheter within the sheath, the sheath being shorter than the inner catheter by an amount at least as great as the length of the offset distal segment of the inner catheter, so that the distal segment of the catheter protrudes distally beyond the distal end of the sheath;
    the sheath having a primary curve of preformed curvature with a radius of curvature larger than that of the secondary curve;
    the sheath and inner catheter being flexible with respect to each other such that when the catheter is inserted into the sheath the catheter enlarges the radius of curvature of the primary curve relative to the preformed curvature and the inner catheter and the sheath bend each other allowing the overall curvature of the assembly to be varied by adjusting the position of the sheath relative to the inner catheter;
    the inner catheter being rotatable relative to the sheath to enable the orientation of the distal tip segment of the inner catheter to be controllably adjusted, wherein the sheath and the catheter assembly assume configurations permitting intubation of both right and left coronary artery ostia by said positioning and rotating of the catheter relative to the sheath.

2. A variable shaped angiography catheter assembly comprising:
    a flexible elongated inner cather having a proximal end and a distal end and a distal portion formed to define a relatively small radius secondary curve and an offset distal tip segment distally of the secondary curve;
    a flexible sheath having a proximal end and a distal end and an internal diameter adapted to receive the inner catheter and to enable longitudinal movement and rotation of the inner catheter within the sheath, the sheath being shorter than the catheter by an amount of at least as great as the length of the offset distal segment of the catheter;

the sheath having a preformed large radius primary curve as compared to the catheter secondary curve formed therein;

the sheath and inner catheter having a degree of flexibility with respect to each other such that when the sheath is positioned over a straight portion of the inner catheter, the curvature of said outer sheath assumes a larger radius of curvature relative to the preformed curvature, wherein the inner catheter and the outer sheath assume configurations permitting intubation of both right and left coronary ostia by adjusting and rotating the inner catheter with respect to the outer sheath.

3. A catheter assembly as defined in either of claims 1 or 2 further comprising:

the catheter having a lumen extending from its proximal to its distal end and being open at its distal end and a fitting on the proximal end of the catheter in communication with the proximal end of the lumen for connection to a fluid instrumentality.

4. A catheter assembly as defined in either of claims 1 or 2 wherein said catheter assembly defines generally a Judkins left curve formed in the distal portion.

5. A catheter assembly as defined in either of claims 1 or 2 further comprising:

the internal diameter of the sheath being greater than the outer diameter of the catheter thereby to define an annular space extending along the length of the assembly;

the distal tip of the sheath being tapered to merge smoothly with and to contact the outer diameter of the catheter;

at least one side hole formed at the distal portion of the sheath;

a fitting at the proximal end of the sheath in communication with the annular flow space for connection to a fluid instrumentality.

6. A catheter assembly as defined in either of claims 1 or 2 further comprising;

a fitting on the proximal end of the sheath, the catheter extending through the fitting, the fitting having a gasket adapted to contact and seal the periphery of the catheter.

7. A catheter assembly as defined in claim 6 wherein the seal is adjustable thereby to vary the degree with which the gasket seals against the catheter.

8. A variable shape catheter assembly as defined in either of claims 1 or 2 wherein the sheath is dimensioned so that it contacts the outer surface of the catheter in close sliding contact therewith.

9. A catheter assembly as defined in claim 8 wherein the sheath is formed from a low friction polymeric material.

10. A catheter assembly as defined in either of claims 1 or 2 wherein the inner catheter is approximately 125 cm long and the sheath is approximately 110 cm long.

11. A catheter assembly as defined in claim 10 wherein the catheter assembly is formed to define generally a Judkin's left shape.

12. A method of performing a left and right coronary angiographic catheterization comprising:

a) providing a catheter assembly comprising:

a flexible elongated inner catheter having a proximal end and a distal end, the catheter having a secondary curve formed at its distal end to define an offset distal tip segment;

a flexible tubular sheath having a proximal end and a distal end and an internal diameter adapted to receive the inner catheter and to enable longitudinal movement of the inner catheter within the sheath, the sheath being shorter than the inner catheter by an amount at least as great as the length of the offset distal segment of the inner catheter, so that the distal segment of the catheter protrudes distally beyond the distal end of the sheath;

the sheath having a primary curve of preformed curvature with a radius of curvature larger than that of the secondary curve;

the sheath and inner catheter being flexible with respect to each other such that when the catheter is inserted into the sheath the catheter enlarges the radius of curvature of the primary curve relative to the preformed curvature and the inner catheter and the sheath bend each other allowing the overall curvature of the assembly to be varied by adjusting the position of the sheath relative to the inner catheter;

the inner catheter being rotatable relative to the sheath to enable the orientation of the distal tip segment of the inner catheter to be controllably adjusted;

b) inserting said catheter assembly into a patient's cardiovascular system;

c) positioning the assembly in a selected location to cause the distal end of the catheter to assume one configuration with the catheter in that curve being adapted to perform a first left or right coronary angiographic catheterization procedure;

d) while maintaining the catheter in said first configuration, performing said first left or right coronary artery catheterization procedure;

e) thereafter shifting the position of the sheath with respect to the catheter thereby to change the configuration of the catheter assembly at the distal region of the catheter to a second configuration and rotating the inner catheter so as to reorient the distal segment of the inner catheter, the second configuration being adapted to perform a second catheterization procedure on the other of said left or right coronary arteries, and f) while maintaining said catheter assembly in said second configuration, performing said other of said catheterization procedures.

13. A method for performing an angiographic catheterization on the right and left coronary arteries comprising:

a) providing a catheter assembly comprising:

a flexible elongated inner catheter having a proximal end and a distal end and a distal portion formed to define a relatively small radius secondary curve and an offset distal tip segment distally of the secondary curve;

a flexible sheath having a proximal end and a distal end and an internal diameter adapted to receive the inner catheter and to enable longitudinal movement and rotation of the inner catheter within the sheath, the sheath being shorter than the catheter by an amount at least as great as the length of the offset distal segment of the catheter;

the sheath having a preformed large radius primary curve as compared to the catheter secondary curve formed therein;

the sheath and inner catheter having a degree of flexibility with respect to each other such that when the sheath is positioned over a straight portion of the inner catheter, the curvature of said outer sheath assumes a larger radius of curvature relative to the preformed curvature, b) inserting said catheter assembly into a patient's cardiovascular system;

c) positioning the assembly in a selected location to cause the distal end of the catheter to assume one configuration with the catheter in that curve being adapted to perform a first left or right coronary angiographic catheterization procedure;

d) while maintaining the catheter in said first configuration, performing said first left or right coronary artery catheterization procedure;

e) thereafter shifting the position of the sheath with respect to the catheter thereby to change the configuration of the catheter assembly at the distal region of the catheter to a second configuration and rotating the inner catheter so as to reorient the distal segment of the inner catheter, the second configuration being adapted to perform a second catheterization procedure on the other of said left or right coronary arteries, and f) while maintaining said catheter assembly in said second configuration, performing said other of said catheterization procedures.

14. A method as defined in either of claims 12 or 13 wherein one of said catheterization procedures comprises intubating the distal tip of the inner catheter into one of the right or left coronary ostia and the second catheterization procedure includes intubating the distal tip of the inner catheter into the other of the right or left coronary ostia.

15. A method as defined in either of claims 12 or 13 wherein said sheath and catheter define an annular lumen extending along the length of the sheath, the sheath having a proximal fitting for connection of a fluid device thereto, the procedure further comprising causing fluid to flow through the annular space defined between the sheath and the catheter.

16. A method of performing an angiographic catheterization procedure on the right and left coronary arteries comprising:

a) providing a catheter assembly comprising:
a flexible elongated inner catheter having a proximal end and a distal end, the catheter having a secondary curve formed at its distal end to define an offset distal tip segment;

a flexible tubular sheath having a proximal end and a distal end and an internal diameter adapted to receive the inner catheter and to enable longitudinal movement of the inner catheter within the sheath, the sheath being shorter than the inner catheter by an amount at least as great as the length of the offset distal segment of the inner catheter, so that the distal segment of the catheter protrudes distally beyond the distal end of the sheath;

the sheath having a primary curve of preformed curvature with a radius of curvature larger than that of the secondary curve;

b) inserting said catheter assembly into a patient's cardiovascular system so that the distal portion of the catheter assembly extends over the aortic arch and generally towards the right or left coronary ostia;

c) positioning said outer sheath on the inner catheter so that the distal segment of the outer sheath points generally toward one of said right or left coronary ostia and manipulating the inner catheter to insert the tip of the inner catheter into said ostia;

d) while maintaining said position and configuration of the catheter assembly, performing an angiographic study of the coronary artery associated with that coronary ostium;

e) shifting the position of the sheath with respect to the inner catheter to direct the distal segment of the outer sheath toward the other of said right or left coronary ostia and rotating the inner catheter so that its distal tip segment is directed to said other coronary ostia and causing the tip to intubate the said other coronary ostia;

f) while maintaining said second configuration, performing an angiographic study on the coronary arteries leading from the said other ostia.

17. A method for performing an angiographic catheterization in the right and left coronary arteries comprising:

a) providing a catheter assembly comprising:
a flexible elongated inner catheter having a proximal end and a distal end and a distal portion formed to define a relatively small radius secondary curve and an offset distal tip segment distally of the secondary curve;

a flexible sheath having a proximal end and a distal end and an internal diameter adapted to receive the inner catheter and to enable longitudinal movement and rotation of the inner catheter within the sheath, the sheath being shorter than the catheter by an amount at least as great as the length of the offset distal segment of the catheter;

the sheath having a preformed large radius primary curve as compared to the catheter secondary curve formed therein;

the sheath and inner catheter having a degree of flexibility with respect to each other such that when the sheath is positioned over a straight portion of the inner catheter, the curvature of said outer sheath assumes a larger radius of curvature relative to the preformed curvature;

b) inserting said catheter assembly into a patient's cardiovascular system so that the distal portion of the catheter assembly extends over the aortic arch and generally towards the right or left coronary ostia;

c) positioning said outer sheath on the inner catheter so that the distal segment of the outer sheath points generally toward one of said right or left coronary ostia and manipulating the inner catheter to insert the tip of the inner catheter into said ostia;

d) while maintaining said position and configuration of the catheter assembly, performing an angiographic study of the coronary artery associated with that coronary ostium;

e) shifting the position of the sheath with respect to the inner catheter to direct the distal segment of the outer sheath toward the outer of said right or left coronary ostia and rotating the inner catheter so that its distal tip segment is directed to said other coronary ostia and causing the tip to intubate the said other coronary ostia;

f) while maintaining said second configuration, performing an angiographic study on the coronary arteries leading from the said other ostia.

18. A method as defined in either of claims 15 or 17 wherein the step of shifting the position of the sheath comprises relocating the secondary bend of the catheter assembly to a different proximal position.

* * * * *